(12) United States Patent
Nie et al.

(10) Patent No.: US 11,119,026 B2
(45) Date of Patent: Sep. 14, 2021

(54) CALIBRATION METHOD AND SYSTEM FOR A LUBRICATION OIL METAL DEBRIS SENSOR

(71) Applicant: FATRI United Testing & Control Technologies Co., Ltd., Quanzhou (CN)

(72) Inventors: Yongzhong Nie, Quanzhou (CN); Jianhai Qiu, Quanzhou (CN)

(73) Assignee: Fatri United Testing & Control (Quanzhou) Technologies Co., Ltd, Quanzhou (CN)

(*) Notice: Subject to any disclaimer, the term of this patent is extended or adjusted under 35 U.S.C. 154(b) by 144 days.

(21) Appl. No.: 16/459,862

(22) Filed: Jul. 2, 2019

(65) Prior Publication Data
US 2020/0096431 A1  Mar. 26, 2020

(30) Foreign Application Priority Data

Sep. 20, 2018 (CN) .......................... 201811102188.5

(51) Int. Cl.
*G01N 15/10* (2006.01)
*G01N 33/28* (2006.01)
(Continued)

(52) U.S. Cl.
CPC ......... *G01N 15/1012* (2013.01); *F16N 29/04* (2013.01); *G01N 15/1031* (2013.01); *G01N 33/2888* (2013.01); *G01N 2015/1087* (2013.01)

(58) Field of Classification Search
CPC .... G01D 18/00; G01D 18/008; G01N 21/274; G01N 30/8665; G01N 35/00693;
(Continued)

(56) References Cited

U.S. PATENT DOCUMENTS

| | | |
|---|---|---|
| 5,150,036 A | 9/1992 | Pourprix |
| 5,604,441 A | 2/1997 | Freese, V et al. |
| | (Continued) | |

FOREIGN PATENT DOCUMENTS

| | | |
|---|---|---|
| CN | 102608008 A | 7/2012 |
| CN | 102818754 A | 12/2012 |
| | (Continued) | |

OTHER PUBLICATIONS

South China University of Technology; "Research of Detection of Lubricants Metal Particles"; Gong Di; pp. 1-8.
(Continued)

*Primary Examiner* — Daniel S Larkin
*Assistant Examiner* — Anthony W Megna Fuentes
(74) *Attorney, Agent, or Firm* — Taft Stettinius & Hollister LLP; Stephen F. Rost

(57) ABSTRACT

A calibration method and system for a lubrication oil metal debris sensor includes applying an excitation to the lubrication oil metal debris sensor to be calibrated, obtaining a second output signal from the lubrication oil metal debris sensor to be calibrated based on a test metal ball with a known diameter, and determining a sensitivity characteristic parameter of the lubrication oil metal debris sensor to be calibrated according to the diameter of the test metal ball with the known diameter, the second output signal, and a preset data processing model. Large particulate metal balls with large diameter are used as calibration particles. The calibration performed by the combination of the particulate metal ball and the data processing model helps when the signal processing circuit cannot be matched with the actual performance of the sensor and avoids an underestimation of the monitoring capability of the lubrication oil metal debris sensor.

16 Claims, 2 Drawing Sheets

(51) Int. Cl.
  *F16N 29/04* (2006.01)
  *F01M 11/10* (2006.01)
  *G01N 15/00* (2006.01)
  *G01N 15/06* (2006.01)
  *G01D 18/00* (2006.01)

(58) Field of Classification Search
  CPC ........... G01N 15/1012; G01N 15/1031; G01N 33/2888; G01N 2015/1087; G01N 2015/0053; G01N 15/0656; F16N 29/04; F01M 11/10; F01M 2011/144
  See application file for complete search history.

(56) References Cited

U.S. PATENT DOCUMENTS

| | | |
|---|---|---|
| 2018/0217046 A1 | 8/2018 | Marra |
| 2020/0056975 A1 | 2/2020 | Nie et al. |

FOREIGN PATENT DOCUMENTS

| | | |
|---|---|---|
| CN | 203249845 U | 10/2013 |
| CN | 203249854 U | 10/2013 |
| CN | 203365278 U | 12/2013 |
| CN | 104215557 A | 12/2014 |
| CN | 204831977 U | 12/2015 |
| CN | 205246651 U | 5/2016 |
| CN | 106769724 A | 5/2017 |
| CN | 206248112 U | 6/2017 |
| CN | 107505237 A | 12/2017 |
| CN | 107560978 A | 1/2018 |
| CN | 107709965 A | 2/2018 |
| CN | 107907455 A | 4/2018 |
| CN | 108008453 A | 5/2018 |
| EP | 0445022 A3 | 2/1991 |
| EP | 2793023 A1 | 10/2014 |
| WO | 2016076945 A1 | 5/2016 |

OTHER PUBLICATIONS

Notification of First Office Action of Priority CN Application No. 2018111021885; dated Jul. 21, 2020; pp. 1-8.
Notification of Second Office Action, Chinese Patent Application No. 2018111021885, dated Dec. 11, 2020, China National Intellectual Property Administration, 7 pages.
State Intellectual Property Office of the People's Republic of China; Decision of Refusal of Corresponding CN Application No. 201811102188.5; pp. 1-8; dated Apr. 7, 2021.

CALIBRATION METHOD AND SYSTEM FOR A LUBRICATION OIL METAL DEBRIS SENSOR

CROSS REFERENCE TO RELATED APPLICATIONS

This application claims priority to Chinese Patent Application No. 201811102188.5, filed on Sep. 20, 2018, the entire contents of which are incorporated herein by reference.

FIELD OF THE DISCLOSURE

The present application relates to the field of wear and fault diagnosis and detection for an equipment, and particularly relates to a calibration method and system for a lubrication oil metal debris sensor.

BACKGROUND

In order to reduce wear and tear during the operation of engines, bearings, gears, etc., a lubrication oil system is usually adopted. Experiences show that there is a strong correlation between damage degree of wear parts of equipment (such as engines, rolling bearings, gears, etc.) and particles in the lubrication system. Therefore, in order to evaluate equipment wear, a lubrication oil metal debris sensor is usually installed in the lubrication oil system. The lubrication oil metal debris sensor must be able to distinguish tiny particles, in order to monitor the entire wear process of the equipment. Presumably, the metal particles are spherical, and the diameters of the metal particles are supposed to be within the range of tens to hundreds of microns, Tiny particulate metal debris causes great difficulty for calibrating the metal debris sensor, For example, firstly, it is difficult to obtain standard tiny metal balls; secondly, different sizes of metal particles are required in order to accurately calibrate the sensor, which requires a wide variety of metal balls; thirdly, the metal particles are prone to agglomerate when they are in small size, and it is difficult to disperse them and let them pass through the inner tube of the sensor one by one, such that the quantitative calibration for the lubrication oil metal debris sensor cannot be realized; finally, the resolving power of the lubrication oil metal debris sensor cannot be matched with signal processing circuits, resulting in an underestimation of the actual performance for a designed sensor.

SUMMARY

Therefore, the present application provides a calibration method and system for a lubrication oil metal debris sensor, which overcomes the deficiencies in the prior art that the it is easy to misjudge the performance of the lubrication oil metal debris sensor such that the lubrication oil metal debris can be conveniently and quickly calibrated.

The embodiment the present application provides a method for calibrating a lubrication oil metal debris sensor, comprising applying an excitation to the lubrication oil metal debris sensor to be calibrated; obtaining a second output signal from the lubrication oil metal debris sensor to be calibrated based on a test metal ball with a known diameter; determining a sensitivity characteristic parameter of the lubrication oil metal debris sensor to be calibrated according to the diameter of the test metal ball with the known diameter, the second output signal, and a preset data processing model.

The method for calibrating a lubrication oil metal debris sensor described above, further includes obtaining output signal characteristics of the metal balls with different preset diameter ranges according to the preset data processing model and the sensitivity characteristic parameter of the lubrication oil metal debris sensor to be calibrated; building a feature table, as a calibration result, with the output signal characteristics of the metal balls with different preset diameter ranges.

The preset data processing model is constructed by the following steps of collecting a first output signal from the lubrication oil metal debris sensor to be calibrated based on test metal balls preset with different diameters; constructing the preset data processing model of the lubrication oil metal debris sensor according to the test metal balls preset with different diameters and the corresponding first output signal.

The preset data processing model is:

$$E = k r^{a3}$$

wherein, $r^a$ is the diameter of the test metal ball, E is a output voltage of the test metal ball through the lubrication oil metal debris sensor, and k is the sensitivity characteristic parameter.

The method for calibrating a lubrication oil metal debris sensor described above may further include filtering the second output signal, after the step of obtaining the second output signal from the lubrication oil metal debris sensor to be calibrated based on the test metal ball with the known diameter and before the step of determining the sensitivity characteristic parameter of the lubrication oil metal debris sensor to be calibrated according to the diameter of the test metal ball with the known diameter, the second output signal, and the preset data processing model.

The method for calibrating a lubrication oil metal debris sensor described above further comprising amplifying the second output signal, after the step of filtering the second output signal and before the step of determining the sensitivity characteristic parameter of the lubrication oil metal debris sensor to be calibrated according to the diameter of the test metal ball with the known diameter, the second output signal, and the preset data processing model.

The method for calibrating a lubrication oil metal debris sensor described above, further comprising amplifying the second output signal, after the step of obtaining the second output signal from the lubrication oil metal debris sensor to be calibrated based on the test metal ball with the known diameter and before the step of determining the sensitivity characteristic parameter of the lubrication oil metal debris sensor to be calibrated according to the diameter of the test metal ball with the known diameter, the second output signal, and the preset data processing model.

The test metal ball passes through an oil pipeline of the lubrication oil metal debris sensor to be calibrated in a manner of free fall motion or uniform motion.

The embodiment of the present application provides a calibration system for a lubrication oil metal debris sensor, comprising a power module for applying an excitation to the lubrication oil metal debris sensor to be calibrated; a signal collecting module for obtaining a second output signal from the lubrication oil metal debris sensor to be calibrated based on a test metal ball with a known diameter, and a data processing module for determining a sensitivity characteristic parameter of the lubrication oil metal debris sensor to be calibrated according to the diameter of the test metal ball with the known diameter, the second output signal, and a preset data processing model.

The calibration system of the lubrication oil metal debris sensor described above further comprises a calibration result output module for obtaining output signal characteristics of the metal balls with different preset diameter ranges according to the preset data processing model and the sensitivity characteristic parameter of the lubrication oil metal debris sensor to be calibrated and building a feature table, as a calibration result, with the output signal characteristics of the metal balls with different preset diameter ranges.

The technical solution of the present application may have several advantages which are described below and herein. For example, the calibration method and system for the lubrication oil metal debris sensor provided by the application choose large particulate metal balls with large diameter as calibration particles which can be easily obtained at low cost. This greatly saves time, decrease costs and improves techniques. Furthermore, the calibration performed by combination of large particulate metal ball and the data processing model solves the problem that the signal processing circuit cannot be matched with the actual performance of the sensor, and avoids an underestimation of the monitoring capability of the lubrication oil metal debris sensor, thereby providing an input for the signal circuit design and greatly improving the particle resolving ability of the sensor.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

The drawings of the embodiments of the present application or the description of the prior art will be briefly described below in order to more clearly illustrate the embodiments of the present application or the technical solutions in the prior art. The drawings in the following description represent some embodiments of the present application, and other drawings can be obtained based on these drawings by those skilled in the art without paying any inventive labor.

DETAILED DESCRIPTION OF THE EMBODIMENTS

The technical solutions according to the embodiments of the invention will be described below clearly with reference to the drawings in the embodiments of the invention, and apparently the embodiments to be described below are only a part but not all of the embodiments of the invention. Based upon the embodiments here of the invention, all the other embodiments which can occur to those ordinarily skilled in the art without any inventive effort shall fall into the scope of the invention.

In the description of the present application, unless otherwise explicitly stated and defined, the terms "installation", "attached", "connected", "fixed" and the like shall be understood broadly. For example, these terms can be understood as a fixed or detachable connection or an integral connection; a mechanical or electrical connection; a directly connection or an indirect connection through an intermediate medium, or an internal connection of two components, a wireless connection or a wired connection. For those skilled in the art, the specific meanings of the above terms in the present application can be understood according to practical situation.

Further, the technical features involved in the different embodiments of the present application described below may be combined with other features as long as they do not conflict with each other.

Embodiment 1

Figure 1:
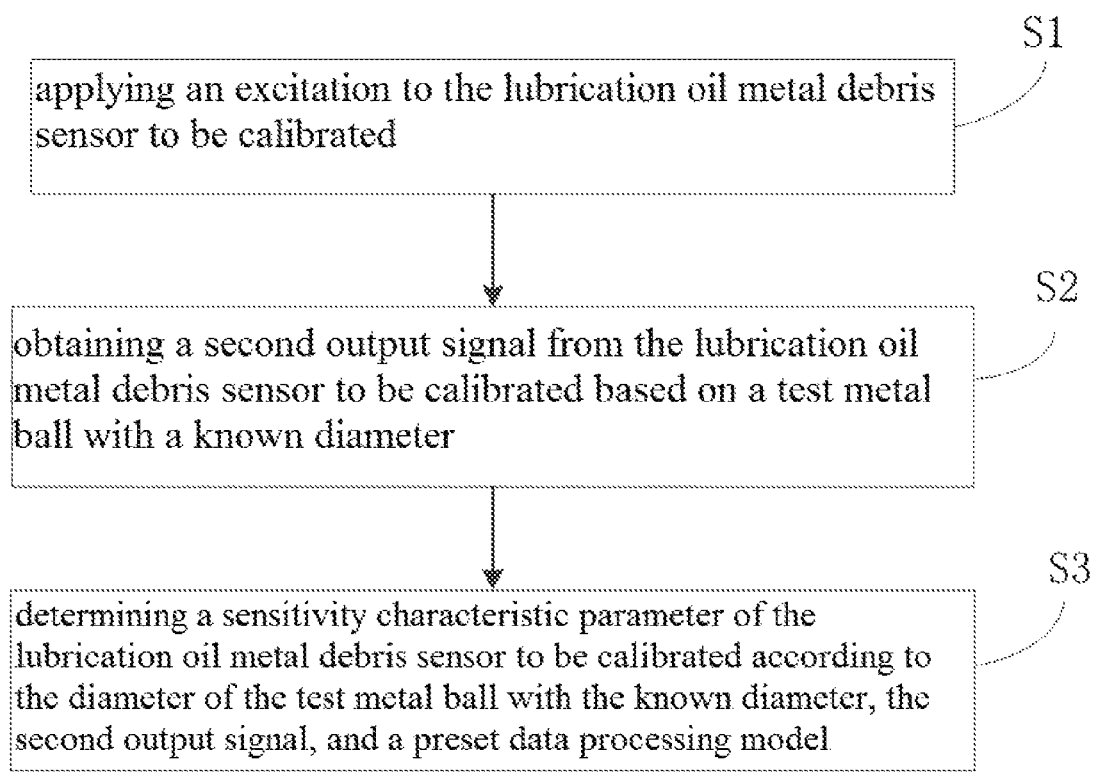
FIG. 1 is a flow chart of a method for calibrating the lubrication oil metal debris sensor according to an embodiment of the present application.

The embodiment of the application provides a method for calibrating the lubrication oil metal debris sensor, as shown in FIG. 1, comprising the following steps:

Step S1: applying an excitation to the lubrication oil metal debris sensor to be calibrated.

In the embodiment of the present application, the calibrated lubrication oil metal debris sensor can be any sensor that uses the inductance-type sensor principle to realize the detection for lubrication oil quality. Regardless of the conventional dual-excitation coil solution or the new even-numbered induction coil solution, and no matter whether the circuit processing module is built-in or external, the method according to the embodiment of the present application can still be used for calibration.

Step S2: obtaining a second output signal from the lubrication oil metal debris sensor to be calibrated based on a test metal ball with a known diameter.

Figure 2:
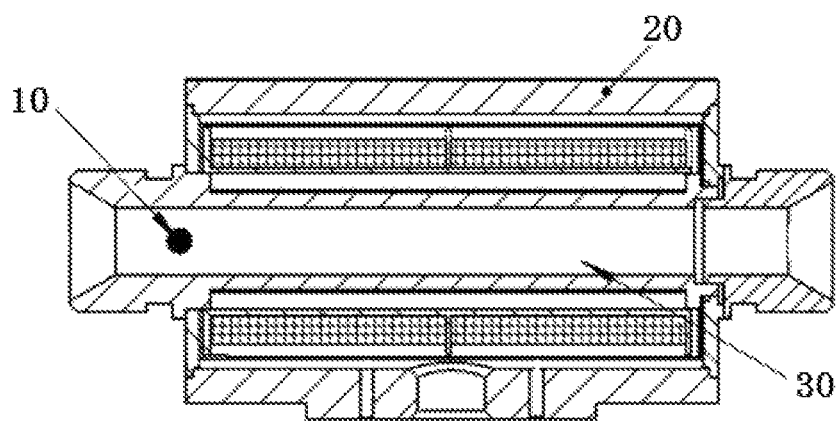
FIG. 2 is a schematic view of a metal ball passing through a lubrication oil metal debris sensor according to an embodiment of the present application.

In the embodiment of the present application, after applying an excitation to the lubrication oil metal debris sensor to be calibrated, as shown in FIG. 2, a standard large particulate metal ball 10 is allowed to pass through the oil pipe 30 of the lubrication oil metal debris sensor 20 to be calibrated And the suitable movement mode of the metal ball should help to achieve convenient and quick calibration for the lubrication oil metal debris sensor, and the metal ball passes through an oil pipeline of the lubrication oil metal debris sensor to be calibrated in a manner of free fall motion or uniform motion according to the environment required by the actual project. The output signal characteristics including the peak-to-peak value of the voltage, pulse width etc. of the lubrication oil metal debris sensor to be calibrated can be obtained with an oscilloscope or other data acquisition system.

In the embodiment of the present application, any large-diameter metal ball that can pass through the oil pipe of the lubrication oil metal debris sensor to be calibrated can be used as a calibration mark, and the selection of the metal ball should follow the principle of ease of being obtained and being at low cost. The metal ball can be made of ferromagnetic materials and non-ferromagnetic materials and the selection of materials should still follow the principle of convenient of being obtained and being at low cost. A commonly used ferromagnetic calibration metal ball can be made of materials including, but are not limited to, cast iron, electrical pure iron, permalloy, low carbon steel, Martensitic stainless steel, etc.; and a commonly used non-ferromagnetic calibration metal ball can be made of materials including, but are not limited to, austenitic stainless steel, aluminum alloy, magnesium alloy, titanium alloy and so on.

Step S3: determining a sensitivity characteristic parameter of the lubrication oil metal debris sensor to be calibrated according to the diameter of the test metal ball with the known diameter, the second output signal, and a preset data processing model.

In the embodiment of the present application, the output signal characteristic of the lubrication oil metal debris sensor obtained above and the diameter of the test metal ball are input into a preset data processing model, and the sensitivity characteristic parameter of the lubrication oil metal debris sensor can be obtained. The ferromagnetic material metal ball and the non-ferromagnetic material metal ball of the same diameter have different sensitivity characteristic parameters corresponding to the lubrication oil metal debris sensor to be calibrated.

In the embodiment of the present application, the preset data processing model may be constructed by the following steps: collecting a first output signal from the lubrication oil metal debris sensor to be calibrated based on test metal balls preset with different diameters; constructing the preset data processing model of the lubrication oil metal debris sensor according to the test metal balls preset with different diameters and the corresponding first output signal.

In the embodiment of the present application, a finite element simulation is performed with a plurality of different preset diameter test metal balls and the corresponding output voltage signals, the data processing model is obtained as:

$$E = k r_a^3$$

wherein, $r_a$ is the diameter of the test metal ball, E is a output voltage of the test metal ball through the lubrication oil metal debris sensor, and k is the sensitivity characteristic parameter.

The data processing model shows that the output voltage of the lubrication oil metal debris sensor is directly proportional to the cube of the radius of the metal ball and the sensitivity characteristic parameters are mainly determined by the excitation voltage, the excitation coil resistance, the excitation coil inductance of each lubrication oil metal debris sensor, and the excitation frequency, specific structural parameters of the lubrication oil metal debris sensor itself comprising the coil number of the excitation coil and the induction coil, the axial length and radius of the excitation coils, and the like to indicate the performance for testing metal ball, so the sensitivity characteristic parameters of each lubrication oil metal debris sensor are different.

In the embodiment of the present application, a ferromagnetic ball with a diameter of 1 mm is compared with a ferromagnetic ball of 600 micrometer diameter in order to verify the conclusion drawn by the data processing model. As shown in Table 1, the deviation of the theoretical value from the measured value is only 2.6%. Therefore, the data processing model can be used to estimate the voltage output of ferromagnetic balls with different diameters passing through the sensor. The reasons that there is a deviation between the theoretical and the measured value are as follows: the ferromagnetic ball is not a standard ball, and the fall position of the ferromagnetic ball is slightly different, the truncation error of the oscilloscope, and the reading error, etc.

TABLE 1

| radius of the ball mm | cube of the radius ratio of the ball | output voltage of the sensor Vpp | output voltage ratio | deviation between cube of radius ratio and output voltage ratio |
|---|---|---|---|---|
| 0.6 | 4.6296 | 6.4 | 4.75 | 2.6% |
| 1 | | 30.4 | | |

Figure 3:
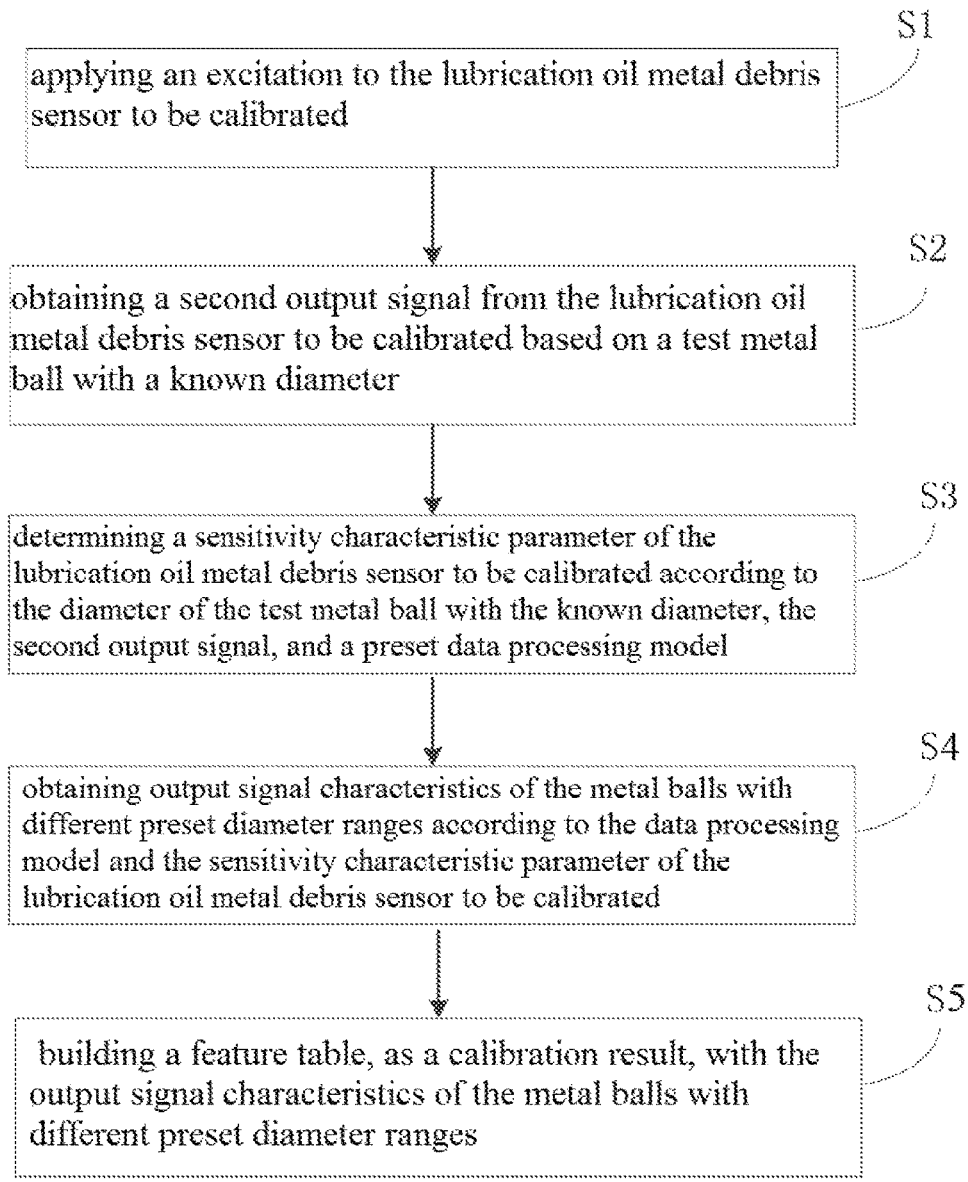
FIG. 3 is a flow chart of a method for calibrating the lubrication oil metal debris sensor according to another embodiment of the present application.

In a further embodiment, as shown in FIG. 3, after performing step S3 the method of calibrating the lubrication oil metal debris sensor described above further comprises the following steps:

Step S4: obtaining output signal characteristics of the metal balls with different preset diameter ranges according to the preset data processing model and the sensitivity characteristic parameter of the lubrication oil metal debris sensor to be calibrated.

In the embodiment of the present application, the output signal characteristics of metal balls with different diameter can be estimated through a built-in MCU, a built-in DSP, a PC end processing, or a manual processing, but not limited thereto, according to a preset data processing model and a sensitivity characteristic parameter of the lubrication oil metal debris sensor to be calibrated.

Step S5: building a feature table, as a calibration result, with the output signal characteristics of the metal balls with different preset diameter ranges.

In the embodiment of the present application, a feature table is built as a calibration result for the lubrication oil metal debris sensor with the output signal characteristics of the metal balls with different preset diameter ranges.

As shown in Table 2, the test metal ball has a diameter of 600 um and the test output voltage is 8.4V. The output voltage of the lubrication oil metal debris sensor is predicted in combination with the preset data processing model when the diameter of the target test metal ball is 50-600 um (but not limited thereto).

TABLE 2

| test voltage Vpp | radius of the test particle μm | diameter of the target test particle μm | estimated output voltage of the sensor Vpp |
|---|---|---|---|
| 8.4 | 600 | 50 | 0.0049 |
| 8.4 | 600 | 75 | 0.0164 |
| 8.4 | 600 | 100 | 0.0389 |
| 8.4 | 600 | 125 | 0.0760 |
| 8.4 | 600 | 150 | 0.1313 |
| 8.4 | 600 | 175 | 0.2084 |
| 8.4 | 600 | 200 | 0.3111 |
| 8.4 | 600 | 225 | 0.4430 |
| 8.4 | 600 | 250 | 0.6076 |
| 8.4 | 600 | 275 | 0.8088 |
| 8.4 | 600 | 300 | 1.0500 |
| 8.4 | 600 | 325 | 1.3350 |
| 8.4 | 600 | 350 | 1.6674 |
| 8.4 | 600 | 375 | 2.0508 |
| 8.4 | 600 | 400 | 2.4889 |
| 8.4 | 600 | 425 | 2.9853 |
| 8.4 | 600 | 450 | 3.5438 |
| 8.4 | 600 | 475 | 4.1678 |
| 8.4 | 600 | 500 | 4.8611 |
| 8.4 | 600 | 525 | 5.6273 |
| 8.4 | 600 | 550 | 6.4701 |
| 8.4 | 600 | 575 | 7.3931 |
| 8.4 | 600 | 600 | 8.4000 |

In another embodiment, the method for calibrating the lubrication oil metal debris sensor described above further comprises amplifying the second output signal for better collecting the output voltage signal after performing step S5 of obtaining a second output signal from the lubrication oil metal debris sensor to be calibrated based on a test metal ball with a known diameter.

In another embodiment, the method for calibrating the lubrication oil metal debris sensor described above further comprises filtering and amplifying the second output signal for better collecting the output voltage signal after performing step S2 of obtaining a second output signal from the lubrication oil metal debris sensor to be calibrated based on a test metal ball with a known diameter.

The method for calibrating the lubrication oil metal debris sensor provided by the application choose large particulate metal balls with large diameter as calibration particles which can be easily obtained at low cost. This greatly saves time, decrease costs and improves techniques. Furthermore, the calibration performed by combination of large particulate metal ball and the data processing model solves the problem that the signal processing circuit cannot be matched with the actual performance of the sensor, and avoids an underestimation of the monitoring capability of the lubrication oil metal debris sensor, thereby providing an input for the signal circuit design and greatly improving the particle resolving ability of the sensor.

Embodiment 2

Figure 4:
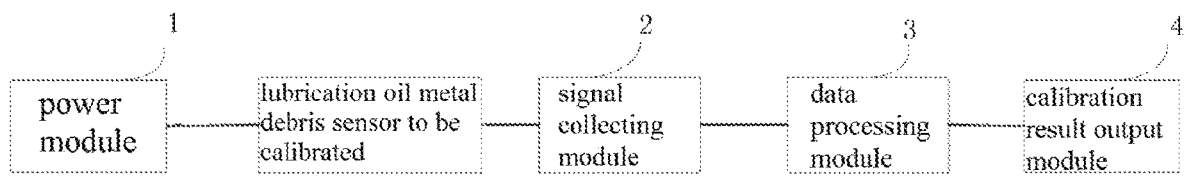
FIG. 4 is a block diagram of a calibration system for the lubrication oil metal debris sensor according to the present application.

A second embodiment of the present application provides a calibration system for a lubrication oil metal debris sensor, as shown in FIG. 4. In this embodiment, the system includes a power module 1 for applying an excitation to the lubrication oil metal debris sensor to be calibrated, wherein the power module performs the method described in step S1 in embodiment 1, and details are omitted; a signal collecting module 2 for obtaining a second output signal from the lubrication oil metal debris sensor to be calibrated based on a test metal ball with a known diameter, wherein said signal collecting module performs the method described in step S2 in embodiment 1, meanwhile filtering and amplifying the second output signal, and details are omitted; a data processing module 3 for determining a sensitivity characteristic parameter of the lubrication oil metal debris sensor to be calibrated according to the diameter of the test metal ball with the known diameter, the second output signal, and a preset data processing model, wherein the said module performs the method described in step S3 in embodiment 1, and details are omitted; a calibration result output module 4 for obtaining output signal characteristics of the metal balls with different preset diameter ranges according to the preset data processing model and the sensitivity characteristic parameter of the lubrication oil metal debris sensor to be calibrated and building a feature table, as a calibration result, with the output signal characteristics of the metal balls with different preset diameter ranges, wherein said module performs the method described in step S4 to step S5 in embodiment 1, and details are omitted.

The calibration system of the lubrication oil metal debris sensor provided by the application choose large particulate metal balls with large diameter as calibration particles which can be easily obtained at low cost. This greatly saves time, decrease costs and improves techniques. Furthermore, the calibration performed by combination of large particulate metal ball and the data processing model solves the problem that the signal processing circuit cannot be matched with the actual performance of the sensor, and avoids an underestimation of the monitoring capability of the lubrication oil metal debris sensor, thereby providing an input for the signal circuit design and greatly improving the particle resolving ability of the sensor.

Those skilled in the art can make various modifications and variations to the invention without departing from the spirit and scope of this disclosure. Thus the invention is also intended to encompass these modifications and variations thereto so long as the modifications and variations come into the scope of the claims appended to the invention and their equivalents.

The invention claimed is:

1. A method for calibrating a lubrication oil metal debris sensor, comprising the following steps:
    applying an excitation to the lubrication oil metal debris sensor to be calibrated;
    obtaining an output signal from the lubrication oil metal debris sensor to be calibrated based on a test metal ball with a known diameter;
    determining a sensitivity characteristic parameter of the lubrication oil metal debris sensor to be calibrated according to the diameter of the test metal ball with the known diameter, the output signal, and a preset data processing model.

2. The method for calibrating a lubrication oil metal debris sensor of claim 1, further comprising:
    obtaining output signal characteristics of metal balls with different preset diameter ranges according to the preset data processing model and the sensitivity characteristic parameter of the lubrication oil metal debris sensor to be calibrated;
    building a feature table, as a calibration result, with the output signal characteristics of the metal balls with different preset diameter ranges.

3. The method for calibrating a lubrication oil metal debris sensor of claim 2, wherein, the test metal ball passes through an oil pipeline of the lubrication oil metal debris sensor to be calibrated in a manner of free fall motion or uniform motion.

4. The method for calibrating a lubrication oil metal debris sensor of claim 1, wherein the preset data processing model is constructed by the following steps:
    collecting another output signal from the lubrication oil metal debris sensor to be calibrated based on test metal balls preset with different diameters;
    constructing the preset data processing model of the lubrication oil metal debris sensor according to the test metal balls preset with different diameters and the corresponding another output signal.

5. The method for calibrating a lubrication oil metal debris sensor of claim 4, wherein, the test metal ball passes through an oil pipeline of the lubrication oil metal debris sensor to be calibrated in a manner of free fall motion or uniform motion.

6. The method for calibrating a lubrication oil metal debris sensor of claim 1, wherein the preset data processing model is:

$$E=kr_a^3$$

Wherein, $r_a$ is the diameter of the test metal ball, E is a output voltage of the test metal ball through the lubrication oil metal debris sensor, and k is the sensitivity characteristic parameter.

7. The method for calibrating a lubrication oil metal debris sensor of claim 6, wherein, the test metal ball passes through an oil pipeline of the lubrication oil metal debris sensor to be calibrated in a manner of free fall motion or uniform motion.

8. The method for calibrating a lubrication oil metal debris sensor of claim 1,
further comprising filtering the output signal, after the step of obtaining the output signal from the lubrication oil metal debris sensor to be calibrated based on the test metal ball with the known diameter and before the step of determining the sensitivity characteristic parameter of the lubrication oil metal debris sensor to be calibrated according to the diameter of the test metal ball with the known diameter, the output signal, and the preset data processing model.

9. The method for calibrating a lubrication oil metal debris sensor of claim 8,
further comprising amplifying the output signal, after the step of filtering the output signal and before the step of determining the sensitivity characteristic parameter of the lubrication oil metal debris sensor to be calibrated according to the diameter of the test metal ball with the known diameter, the output signal, and the preset data processing model.

10. The method for calibrating a lubrication oil metal debris sensor of claim 9, wherein, the test metal ball passes through an oil pipeline of the lubrication oil metal debris sensor to be calibrated in a manner of free fall motion or uniform motion.

11. The method for calibrating a lubrication oil metal debris sensor of claim 8, wherein, the test metal ball passes through an oil pipeline of the lubrication oil metal debris sensor to be calibrated in a manner of free fall motion or uniform motion.

12. The method for calibrating a lubrication oil metal debris sensor of claim 1,
further comprising amplifying the output signal, after the step of obtaining the output signal from the lubrication oil metal debris sensor to be calibrated based on the test metal ball with the known diameter and before the step of determining the sensitivity characteristic parameter of the lubrication oil metal debris sensor to be calibrated according to the diameter of the test metal ball with the known diameter, the output signal, and the preset data processing model.

13. The method for calibrating a lubrication oil metal debris sensor of claim 12, wherein, the test metal ball passes through an oil pipeline of the lubrication oil metal debris sensor to be calibrated in a manner of free fall motion or uniform motion.

14. The method for calibrating a lubrication oil metal debris sensor of claim 1, wherein, the test metal ball passes through an oil pipeline of the lubrication oil metal debris sensor to be calibrated in a manner of free fall motion or uniform motion.

15. A calibration system for a lubrication oil metal debris sensor, comprising:
a power module configured for applying an excitation to the lubrication oil metal debris sensor to be calibrated;
a signal collecting module configured for obtaining an output signal from the lubrication oil metal debris sensor to be calibrated based on a test metal ball with a known diameter, and
a data processing module configured for determining a sensitivity characteristic parameter of the lubrication oil metal debris sensor to be calibrated according to the diameter of the test metal ball with the known diameter, the output signal, and a preset data processing model.

16. The calibration system of the lubrication oil metal debris sensor of claim 15, further comprising:
a calibration result output module configured for obtaining output signal characteristics of metal balls with different preset diameter ranges according to the preset data processing model and the sensitivity characteristic parameter of the lubrication oil metal debris sensor to be calibrated and building a feature table, as a calibration result, with the output signal characteristics of the metal balls with different preset diameter ranges.

* * * * *